(12) United States Patent
Kalchauer et al.

(10) Patent No.: US 7,205,426 B2
(45) Date of Patent: Apr. 17, 2007

(54) PROCESS FOR PREPARING METHYLCHLOROSILANES

(75) Inventors: Wilfried Kalchauer, Burghausen (DE); Jochen Gross, Tuessling (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 11/231,509

(22) Filed: Sep. 21, 2005

(65) Prior Publication Data

US 2006/0063946 A1    Mar. 23, 2006

(30) Foreign Application Priority Data

Sep. 23, 2004  (DE)  .................... 10 2004 046 181

(51) Int. Cl.
*C07F 7/04*  (2006.01)
(52) U.S. Cl. .................................... 556/472
(58) Field of Classification Search .............. 556/472
See application file for complete search history.

(56) References Cited

U.S. PATENT DOCUMENTS 4,645,851 A * 2/1987 Prud'Homme .............. 556/472
4,973,725 A * 11/1990 Lewis et al. ................ 556/472
5,512,662 A   4/1996 Kalchauer et al.
5,625,088 A   4/1997 Kalchauer

FOREIGN PATENT DOCUMENTS

EP   195 728     9/1986
FR   1 037 183   5/1951

OTHER PUBLICATIONS

Derwent Abstract corresponding to EP 195 728 (AN 1986-253674).
Edited by Lewis et al., "Catalyzed Direct Reactions of Silicon," Studies in Organic Chemistry 49, Elsevier 1993, p. 18, Fig. 3.

* cited by examiner

*Primary Examiner*—Thurman K. Page
*Assistant Examiner*—Chukwuma Nwaonicha
(74) *Attorney, Agent, or Firm*—Brooks Kushman P.C.

(57) ABSTRACT

A process for the direct synthesis of methylchlorosilanes by reaction of chloromethane with a contact composition comprising silicon, copper catalyst and from 10 to 90 ppm of strontium leads to increased selectivity and higher production rate.

19 Claims, No Drawings

PROCESS FOR PREPARING METHYLCHLOROSILANES

BACKGROUND OF THE INVENTION

1. Field of the Invention

The invention relates to a process for the direct synthesis of methylchlorosilanes using a contact composition comprising strontium.

2. Background Art

Processes for preparing methylchlorosilanes by reaction of silicon with chloromethane in the direct synthesis by the Müller-Rochow method in the presence of suitable catalysts and catalyst combinations are already known. For example, this is described in "Catalyzed Direct Reactions of Silicon"; K. M. Lewis, D. G. Rethwisch; Elsevier 1993.

In the direct synthesis of methylchlorosilanes, metallic silicon is reacted with chloromethane in the presence of various catalysts and, if desired, promoters, with the target product being dimethyldichlorosilane. The mixture of silicon, catalysts and promoters is referred to as a "contact composition." At present, since over 1,500,000 metric tons per annum of dimethyldichlorosilane are prepared worldwide, small improvements in the production process, for example an increase in the dimethyldichlorosilane selectivity, an increase in the space-time yield specific to dimethyldichlorosilane, or an increase in the specific silicon yield, therefore have a great economic effect.

FR 1037183 and EP 195728 describe the addition of Sr to the contact composition in the direct synthesis. FR 1037183 discloses 1–5% by weight of Sr, while EP 195728 A describes use of Sr in a concentration of from about 0.01 to 2% by weight, with possible catalysts being Cu, CuCl or $CuCl_2$. These high concentrations of Sr have an unfavorable effect on the formation of dimethyldichlorosilane.

SUMMARY OF THE INVENTION

It is an object of the present invention to provide a process for the direct synthesis of methylchlorosilanes by the Müller-Rochow method which improve the preparation of dimethyldichlorosilane. This and other objects are provided by a process for the direct synthesis of methylchlorosilanes wherein chloromethane is reacted with a contact composition comprising silicon, copper catalyst and from 10 to 90 ppm of strontium.

DETAILED DESCRIPTION OF THE PREFERRED EMBODIMENTS

It has been found that a strontium content in the contact composition used for reaction with chloromethane in the direct synthesis, of from 10 to 90 ppm, preferably from 20 to 60 ppm, and in particular from 30 to 50 ppm, has a positive effect on the specific dimethyldichlorosilane formation rate, specifically, the formation of $Me_2SiCl_2$ per mass of silicon used in unit time.

The strontium content of the contact composition is preferably established in a targeted fashion by means of suitable measures. Strontium can be added, for example, as the metal, as an alloy, or as a compound to the contact composition, or is preferably introduced into the contact composition together with the raw materials such as silicon and catalysts. In the latter case, the concentration of Sr in the contact composition is controlled independently of the Sr content of the raw materials via the operating parameters of the methylchlorosilane synthesis. In this case, operating parameters of concern are, for example, the ratio of fresh raw materials fed in, and silicon-containing solids discharged from the system, as described in "Catalyzed Direct Reactions of Silicon"; K. M. Lewis, D. G. Rethwisch; Elsevier 1993", page 18, FIG. 3.

The process can be carried out batchwise or continuously; in industrial production, only the continuous embodiment is employed. "Continuous" means that the amount of silicon reacted and catalysts and promoters discharged in the reaction dust are continually replaced by introduction of further amounts, preferably as a premixed contact composition. The continuous direct synthesis is preferably carried out in fluidized-bed reactors in which chloromethane is used simultaneously as fluidization medium and reactant.

The silicon required is milled to a powder and mixed with copper catalyst and promoters to form the contact composition beforehand. Preference is given to using silicon in a particle size of not more than 700 µm, most preferably in a particle size of not more than 500 µm. The silicon used usually has a purity of >98%.

A production campaign of the continuous direct synthesis is commenced with the induction phase. At the beginning of the induction phase, methyl chloride is fed into the heated contact composition. This is followed by the starter phase in which crude silane formation commences. The reaction initially proceeds with a low selectivity and reactivity. The stable production phase is subsequently achieved. Further amounts of silicon and, if appropriate, catalysts and promoters/cocatalysts are continually introduced. The production campaign ends when no more chloromethane is fed into the contact composition.

During continuous operation of a reactor, the production rates in respect of the target product dimethyldichlorosilane drop after a largely stable production phase in a production campaign. For this reason, the production campaign has to be stopped after a particular time. A production campaign usually extends for from only a few days to a number of weeks. After a production campaign has ended, the reactor is emptied, charged again with silicon, copper catalyst and promoters/cocatalysts and brought back to reaction conditions.

In the direct synthesis, unreacted chloromethane, the gaseous methylchlorosilanes, and entrained particles leave the reactor. The entrained particles comprise partly reacted silicon particles, fine silicon particles, catalysts and promoters/cocatalysts. The entrained particles can, if desired, be separated from the gas stream by means of one or more cyclones, and large entrained particles of contact composition can be returned to the reactor. The silane is subsequently separated off from remaining dust and unreacted chloromethane and passed to a distillation for purification. Purified, unreacted chloromethane can be fed back into the reactor.

The process is preferably carried out in a fluidized-bed reactor, preferably in the temperature range from 250 to 400° C., in particular from 250 to 360° C. The process is usually carried out at the pressure of the surrounding atmosphere, i.e. at from about 0.1 MPa to 0.5 MPa, as these conditions involve the least expense, but higher pressures can also be employed.

Inert gases such as nitrogen or argon can also be used in the process. Preference is given to using no inert gas.

In a preferred embodiment, the gas flow is selected so that a fluidized bed of contact composition and gas is formed in the reactor. Unreacted chloromethane and any inert gas and the gaseous methylchlorosilanes leave the reactor. The contact composition is prepared by simple mixing of the individual components at room temperature. Treatment of the contact composition prior to introduction into the reactor is possible, but is not carried out in the preferred embodiment.

In the process of the invention, (a) the form of the copper is preferably selected from among metallic copper, copper alloys, copper oxide and copper chloride. Copper oxide can, for example, be copper in the form of copper oxide mixtures and in the form of copper(II) oxide. Copper chloride can be used in the form of CuCl or in the form of $CuCl_2$, with corresponding mixtures also being possible. In a preferred embodiment, the copper is used as copper oxide and/or as CuCl.

Preference is given to using from 0.3 to 10% by weight, in particular from 0.5 to 7% by weight of copper catalyst, based on metallic copper and silicon; particular preference is given to from 0.5 to 4.5% by weight.

Promoters can be used in the process of the invention, and are preferably selected from among zinc, phosphorus, cesium, barium, iron, tin and antimony.

Zinc is preferably used in the form of metallic zinc, and also as an alloy with copper, optionally with further promoters, or in the form of zinc oxide or zinc chloride. The amount of zinc used is preferably from 0.05 to 60% by weight, in particular from 0.3 to 40% by weight, based on copper and zinc as metal; particular preference is given to from 0.5 to 10% by weight.

Antimony and/or tin are preferably used together with the zinc, preferably as metals or alloys. The total amount of antimony and/or tin used is preferably from 200 to 8000 ppm, in particular from 300 to 4000 ppm, based on the copper used, calculated as metal; particular preference is given to from 500 to 3000 ppm of antimony and/or tin.

In a preferred embodiment of the process, at least one of the catalyst components copper and zinc is used in a nonmetallic form; particular preference is given to an embodiment in which both catalyst components are used in a nonmetallic form.

In the following examples, unless indicated otherwise in the particular case,
a) all amounts are based on mass;
b) all pressures are 0.10 MPa (abs.);
c) all temperatures are 20° C.

EXAMPLES

The results in the reaction of silicon with chloromethane in the presence of suitable catalysts depend not only on the makeup of the contact composition but also on the structure of the experimental plant and on the experimental conditions. To eliminate the two last-named parameters and to be able to demonstrate the advantages of the invention unambiguously, the experiments described in the following examples were carried out according to the following standardized procedure.

Silicon powder: Commercially available silicon metal containing the following main impurities: Al 0.20%, Fe 0.27%, Ca 0.04%; milled and sieved to a particle size in the range from 70 to 240 μm.

Copper oxide: Prepared as described in U.S. Pat. No. 5,306,328, Example 5.

All other chemicals are commercially available in the chemical trade, e.g. from Fluka Chemie GmbH, Germany.

Experimental Plant:

Laboratory fluidized-bed reactor (vertical glass tube having an internal diameter of 25 mm and a height of 500 mm) provided with heating tape, gas distributor frit, distillation attachment with brine cooling and receiver flask.

Standardized Procedure:

8 mg of tin powder and $SrCl_2.6H_2O$ are intimately mixed, mixed with 120 g of silicon, introduced into the reactor and heated to 340° C. under a stream of nitrogen of 40 l/h. 40 l/h of chloromethane are subsequently passed through the reactor and the contact composition is heated to 395° C. After an induction time in the range from 2 to 30 minutes, silane formation commences, the reaction temperature is reduced to 360° C. and 50 ml of methylchlorosilanes are collected (start phase). A further 30 ml of methylchlorosilanes are subsequently collected. The time taken for these 30 ml of silanes to be formed is referred to as production phase; the production rate (PR2) is calculated according to the equation $$PR2 = \frac{\text{g of methylchlorosilanes in the production phase}}{\text{kg of Si used} \times \text{hours for the production phase}}$$

The specific dimethyldichlorosilane formation rate $(FRM2) =$ $$PR2 \times \frac{\text{concentration of dimethyldichlorosilane in the crude silane}}{100}$$

The silane composition of the 30 ml of methylchlorosilanes was determined in percent by weight by means of GC analysis.

Examples 1 to 4 Not According to the Invention

Amounts of Sr in the contact composition which are too low or too high have a negative effect on the specific dimethyldichlorosilane formation FRM2.

| Example | g [Cu] | ppm [Sr] | PR2 | % of silane M2 | FRM2 |
|---|---|---|---|---|---|
| 1 | 6 g of CuO | 0 | 283 | 81.8 | 231 |
| 2 | 6 g of CuO | 1000 | 205 | 81.8 | 168 |
| 3 | 7.6 g of CuCl | 0 | 336 | 82.2 | 276 |
| 4 | 7.6 g of CuCl | 1000 | 276 | 82.3 | 227 |

Examples 5 to 10

Using copper Cu catalysts, the specific $Me_2SiCl_2$ formation rate FRM2 is increased when Sr is present in an amount in the range according to the invention.

| Example | g [Cu] | ppm [Sr] | PR2 | % of silane M2 | FRM2 |
|---|---|---|---|---|---|
| 5 | 6 g of CuO | 25 | 284 | 82.8 | 235 |
| 6 | 6 g of CuO | 50 | 282 | 84.3 | 238 |
| 7 | 6 g of CuO | 90 | 277 | 83.9 | 232 |
| 8 | 7.6 g of CuCl | 25 | 389 | 86.0 | 335 |
| 9 | 7.6 g of CuCl | 50 | 365 | 86.1 | 314 |
| 10 | 7.6 g of CuCl | 90 | 352 | 86.7 | 305 |

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A process for the direct synthesis of methylchlorosilanes comprising reacting chloromethane with a contact composition comprising silicon, copper catalyst, and from 10 to 90 ppm of strontium based on the weight of the contact composition.

2. The process of claim 1, wherein strontium is introduced into the contact composition with one or both of a silicon raw material or a catalyst raw material.

3. The process of claim 1, wherein at least one form of copper is selected from the group consisting of metallic copper, copper alloys, copper oxide and copper chloride.

4. The process of claim 2, wherein at least one form of copper is selected from the group consisting of metallic copper, copper alloys, copper oxide and copper chloride.

5. The process of claim 1, wherein a zinc promoter is present in said contact composition.

6. The process of claim 2, wherein a zinc promoter is present in said contact composition.

7. The process of claim 3, wherein a zinc promoter is present in said contact composition.

8. The process of claim 5, wherein at least one further promoter selected from the group consisting of tin and antimony are used in addition to zinc.

9. The process of claim 1, wherein strontium is present in an amount of from 20 ppm to 60 ppm.

10. The process of claim 5, wherein strontium is present in an amount of from 20 ppm to 60 ppm.

11. The process of claim 8, wherein strontium is present in an amount of from 20 ppm to 60 ppm.

12. The process of claim 1, wherein strontium is present in an amount of from 60 ppm to 50 ppm.

13. The process of claim 5, wherein strontium is present in an amount of from 60 ppm to 50 ppm.

14. The process of claim 8, wherein strontium is present in an amount of from 60 ppm to 50 ppm.

15. The process of claim 1, wherein copper is added in the form of CuCl.

16. The process of claim 9, wherein copper is added in the form of CuCl.

17. The process of claim 11, wherein copper is added in the form of CuCl.

18. The process of claim 12, wherein copper is added in the form of CuCl.

19. The process of claim 13, wherein copper is added in the form of CuCl.

* * * * *